US00PP13410P3

(12) United States Plant Patent
Strope

(10) Patent No.: US PP13,410 P3
(45) Date of Patent: Dec. 24, 2002

(54) NEW GUINEA IMPATIENS PLANT NAMED 'BALCELBUPI'

(75) Inventor: Kerry M. Strope, Pismo Beach, CA (US)

(73) Assignee: Ball FloraPlant, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 09/772,807

(22) Filed: Jan. 30, 2001

(65) Prior Publication Data

US 2002/0133859 P1 Sep. 19, 2002

(51) Int. Cl.[7] ..... A01H 5/00

(52) U.S. Cl. ..... Plt./318

(58) Field of Search ..... Plt./318

*Primary Examiner*—Bruce R. Campell
*Assistant Examiner*—June Hwu
(74) *Attorney, Agent, or Firm*—Wood, Phillips, Katz, Clark & Mortimer

(57) ABSTRACT

A new and distinct New Guinea impatiens cultivar named Balcelbupi, characterized by its large blush pink flowers, dark green foliage, compact upright and mounded habit and excellent basal branching.

1 Drawing Sheet

BACKGROUND OF INVENTION

The present invention comprises a new and distinct New Guinea impatiens plant, botanically known as *Impatiens hawkeri,* and hereinafter referred to by the cultivar name 'Balcelbupi'.

The new cultivar was developed by the inventor in a controlled breeding program during 1997 at Arroyo Grande, Calif. The objective of the breeding program was to develop new cultivars with numerous, large flowers, excellent basal branching and upright medium growth habit.

The female (seed) parent of 'Balcelbupi' was 'Moorea' (U.S. Plant Pat. No. 9,147) characterized by its compact growth habit, pure white flowers and medium green foliage. The male (pollen) parent of 'Balcelbupi' was the proprietary *Impatiens hawkeri* cultivar designated '50-4' (non-patented) characterized by its compact habit, pink flowers and dark green foliage. 'Balcelbupi' was discovered and selected as a flowering plant within the progeny of the stated cross in December of 1997.

Asexual reproduction of the new cultivar by terminal cuttings has demonstrated that the characteristics of the new cultivar as herein described are firmly fixed and retained through successive generations of such asexual propagation. The new cultivar was asexually reproduced in Arroyo Grande, Calif. and West Chicago, Ill.

SUMMARY OF INVENTION

It was found that the cultivar of the present invention:
(a) Exhibits large round blush pink flowers,
(b) Forms dark green foliage,
(c) Exhibits a good basal branching character, and
(d) Exhibits a medium, upright mounded growth habit.

The new cultivar of the present invention can be compared to both its female parent 'Moorea' and Celebration Blush White (U.S. Plant Pat. No. 8,538). When compared to 'Moorea' it is found that the new cultivar has larger flowers, smaller leaves, longer internodes and shorter spur. When compared to Celebration Blush White, the new cultivar is more compact, has shorter internodes, smaller leaves and larger flowers of a darker pink color. A detailed comparison can be found in Table A, below.

Distinctive Characteristics:

| Characteristic | 'Goldenglossy' | 'Sherwoodii' | 'Conti' | 'Sunrise' |
|---|---|---|---|---|
| Height (Mature) | 3–4' | 3–4' | 1 ½'–2' | 3–4' |
| Width (Mature) | 4–5' | 4–5' | 4–5' | 4–5' |
| Growth Habit | Compact | Compact | Ground cover | Compact |
| Leaf Length | ¾–1 ¼" | ¾–1 ¼" | ¾–1" | ¾–1" |
| Leaf Width | ⅜–⅝" | ⅜–⅝" | ⅜–⅝" | 5/16–½" |
| Leaf Variegation (Immature) | Yellow Group 10B | None | Greyed-Yellow G.160C | Greyed-Yellow G.160A |
| Leaf Variegation (Mature) | Yellow-Green G.144A | None | Greyed-Yellow G.160C | Greyed-Yellow G.160A |

BRIEF DESCRIPTION OF THE PHOTOGRAPH

The accompanying photographs show as nearly true as it is reasonably possible to make the same in color illustrations of this type, typical flower and foliage characteristics of the new cultivar. The plants were grown in a greenhouse at West Chicago, Ill., U.S.A.

DETAILED DESCRIPTION

The 'Balcelbupi' cultivar has not been observed under all possible environmental conditions to date. Accordingly, it is possible that the phenotype may vary somewhat with variations in the environment, such as temperature, light intensity, and day length.

The chart used in the identification of colors described herein is The R.H.S. Colour Chart of The Royal Horticultural Society, London, England. The color values were determined on Aug. 30, 2000 between 1:00 and 1:45 p.m. under natural daylight conditions. The following measurments and describe plants ten (10) weeks old and produced from cuttings taken from stock plants and grown in 10 cm pots under greenhouse conditions comparable to those used in commercial practice while utilizing a soilless growth medium and maintaining temperatures of approximately 72° F. during the day and approximately 65° F. during the night.

Classification:

*Botanical.*—*Impatiens hawkeri* cultivar 'Balcelbupi'.

Parentage: 'Moorea' (seed)×Proprietary seedling '50-4' (pollen).

Propagation:

*Type cutting.*—Terminal tip.

*Time to initiate roots.*—Approximately 7–14 days with the shorter times generally being experienced in the summer and the longer times in the winter.

*Time to develop roots.*—Approximately 21 days.

*Rooting habit.*—Fibrous, branching.

Plant description:

*Habit of growth.*—Moderately vigorous with good basal branching. A mature plant, 8 to 10 weeks after the planting of a rooted cutting, commonly measures approximately 18.4 cm in height and approximately 29 cm in width.

*Plant form.*—Upright and mounded.

*Foliage.*—Shape: Lanceolate; acuminate apex; attenuate base; ciliate and serrate margin Texture: Smooth, slightly pubescent on upper surface only. Size of mature foliage: Approximately 6.8 cm in length; approximately 1.9 cm in width. Color of mature foliage: Upper surface is 139A, with mid vein lighter than 53D; Lower surface is 137C with veins of 53C Petiole: Length: approximately 6 mm, Color: 53D.

*Stem.*—Color178A. Internode length: Approximately 5.2 cm.

Flower description:

*Flowering habit.*—Freely flowering.

*Natural flowering season.*—Year round in greenhouse environment. Flowering is continuous from spring until fall in the garden.

*Bud shape, color.*—Bud Shape: Ovate. Color: 55C.

*Flowers borne.*—Above foliage arising from leaf axils.

*Quantity of flowers.*—Approximately 1 flower and 4 buds per stem.

*Flower size.*—Approximately 7.1 cm in diameter.

*Flower buds.*—Length: approximately 2.1 cm. Width: approximately 1.3 cm.

*Petals.*—Number: Five, overlapping. Size: Superior petal length — 3.3 cm, superior petal width — 5.2 cm. Lateral petal length — 3.7 cm, lateral petal width — 3.4 cm. Lower petal length — 4.2 cm, lower petal width — 4.3 cm. Shape: obcordate with emarginate apex attenuate base and entire margin. Texture: smooth and irridescent.

*Flower color.*—Light Pink. Upper surface of petals has a background of 73D with fine venation of 73B overall and bases of 73A forming an "eye"; lower surface has background of 73D, fine venation overall of 73B, midveins and bases of 61B.

*Spur.*—Length: Approximately 4.7 cm. Shape: Sharply curved. Color: 60B.

*Peduncles.*—Length approximately 4.3 cm. Color: 178B.

*Reproductive organs.*—Androecium: Five stamens. Anther size: Approximately 2.5 mm. Color: 39D. Anthers are fused together forming one organ that surrounds the pistil. Generally, the anthers shed pollen prior to the stigma becoming receptive. Pollen color: 19D. Gynoecium: Pistil number: One. Stigma length: >1 mm. Stigma color: 154D. Style length: 1 mm. Style color: 144A. Ovary length: 4 mm. Ovary color: 144A.

*Seed development.*—Seed production has not been observed.

*Disease resistance.*—Resistance to pathogens has not been observed.

I claim:

1. A new and distinct cultivar of New Guinea impatiens plant named 'Balcelbupi' substantially as herein shown and described, which:

(a) Exhibits large round blush pink flowers,
(b) Forms dark green foliage,
(c) Exhibits a good basal branching character, and
(d) Exhibits an upright mounded growth habit.

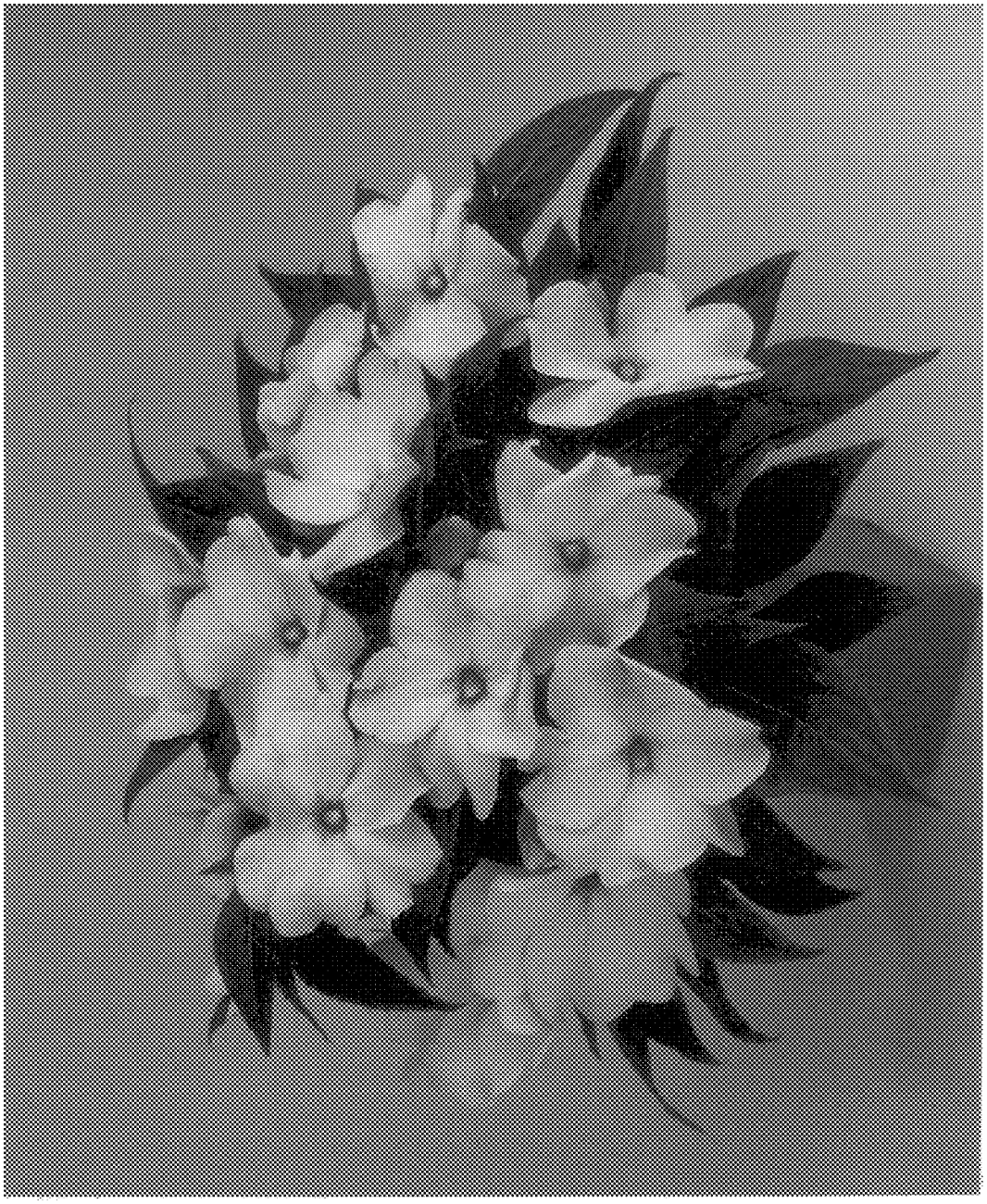

* * * * *